(12) United States Patent
Heck et al.

(10) Patent No.: US 8,338,122 B2
(45) Date of Patent: Dec. 25, 2012

(54) METHOD FOR DETERMINING THE AMINO ACID SEQUENCE OF PEPTIDES

(75) Inventors: Albert John Roeland Heck, Utrecht (NL); Shabaza Mohammed, Utrecht (NL); Bastiaan Van Breukelen, Utrecht (NL); Nadia Taouatas, Utrecht (NL); Madalina Mihaela Drugan, Utrecht (NL)

(73) Assignee: U-Protein Express B.V., Houten (NL)

( * ) Notice: Subject to any disclaimer, the term of this patent is extended or adjusted under 35 U.S.C. 154(b) by 271 days.

(21) Appl. No.: 12/735,373

(22) PCT Filed: Jan. 14, 2009

(86) PCT No.: PCT/EP2009/050365
§ 371 (c)(1), (2), (4) Date: Jul. 9, 2010

(87) PCT Pub. No.: WO2009/090188
PCT Pub. Date: Jul. 23, 2009

(65) Prior Publication Data
US 2010/0311098 A1    Dec. 9, 2010

(30) Foreign Application Priority Data
Jan. 15, 2008    (EP) .................................. 08150294

(51) Int. Cl.
*C12Q 1/34*    (2006.01)
(52) U.S. Cl. ......................................................... 435/18
(58) Field of Classification Search ........................ None
See application file for complete search history.

(56) References Cited

U.S. PATENT DOCUMENTS
2004/0121477 A1    6/2004    Thompson et al.
2006/0014210 A1    1/2006    Boyes et al.

FOREIGN PATENT DOCUMENTS
EP          1 617 223 A1      1/2006
WO       WO 02/08767 A2      1/2002
WO       WO 2009/090188 A1   7/2009

OTHER PUBLICATIONS

Rao et al. J. Proteome Res. Proteolytic 18O labeling by peptidyl-lys metalloendopeptidase for comparative proteomics. (2005) 4, 507-514.*
Dormeyer et al., Targeted Analysis of Protein Termini, Journal of Proteome Research, 2007. pp. 4634-45. vol. 6.
Pinkse et al.. Highly Robust, Automated, and Sensitive Online $TiO_2$-Based Phosphoproteomics Applied to Study Endogenous Phosphorylation in Drosophila melanogaster, Journal of Proteome Research. 2008, pp. 687-697. vol. 7. No. 2.
Syka et al., Peptide and protein sequence analysis by electron transfer dissociation mass spectrometry. PNAS. Jun. 29, 2004. pp. 9528-9533, vol. 101, No. 26.
Van Breukelen et al., Resolving stiochiometries and oligomeric states of glutamate synthase protein complexes with curve fitting and simulation of electrospray mass spectra, Rapid Communications in Mass Spectrometry, 2006. pp. 2490-2496. vol. 20. No. 16.
PCT International Search Report, PCT/EP2009/050365 dated May 13, 2009.
PCT International Preliminary Report on Patentability for Application No. PCT/EP2009/050365, dated Jul. 20, 2010, 7 pages.

* cited by examiner

*Primary Examiner* — Nashaat Nashed
(74) *Attorney, Agent, or Firm* — TraskBritt

(57) ABSTRACT

The invention is in the field of analytical methods suitable for biochemical applications and provides a method for determining the amino acid sequence of a peptide. The determination of amino acid sequences of proteins and peptides is useful in the study of biological systems. The invention relates to a method for determining at least part of the amino acid sequence of a protein comprising the steps of cleaving the protein into proteolytic peptides, ionizing the proteolytic peptides to generate peptide precursor ions, dissociating these peptide precursor ions using tandem mass spectrometry in order to obtain peptide fragment ions, followed by determining the amino acid sequence of a selected proteolytic peptide wherein the cleaving step generates at least one proteolytic peptide with an N-terminal lysine residue and wherein the dissociation of the peptide precursor ions is initiated by electron transfer.

11 Claims, 6 Drawing Sheets

A3  GADFLVTEVENGGSLGSK

B3  KGADFLVTEVENGGSLGS

Figure 6

Figure 1:
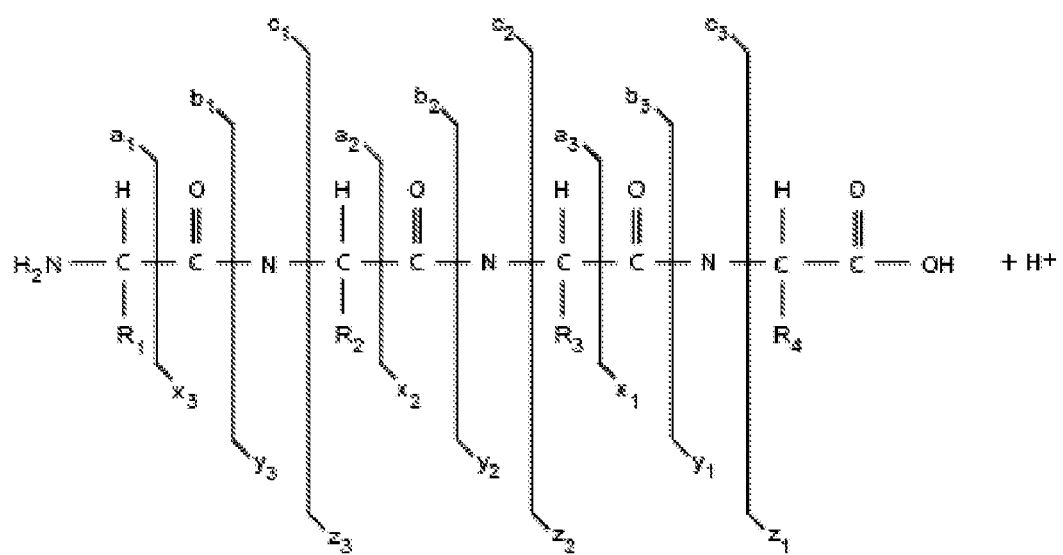

SEQ ID NO: 1:

```
TYNGCSSSEQSALAAAASAAQSYVAESLSYLQTHTAATPRYTTWFGSYISSRHSTVLQH
YTDMNSNDFSSYSFDCTCTAAGTFAYVYPNRFGTVYLCGAFWKAPTTGTDSQAGTLVHES
SHFTRNGGTKDYAYGQAAAKSLATMDPDKAVMNADNHEYFSENNPAQS
```

SEQ ID NO: 2

```
ATFVGCSATRQTQLNAAASQAQTYAANALSYLNSHTSSTTRYTTWFGTFVTSRYNTVLSH
FSSISSNTFSSYTFDCTCSDSGTYAFVNPSNFGYVTLCGAFWNAPVAGTDSRGGTLIHES
SHFTRNGGTDDHVYGQAGAQSLARSNPAQAIDNADSHEYFAENNPALA
```

METHOD FOR DETERMINING THE AMINO ACID SEQUENCE OF PEPTIDES

FIELD OF THE INVENTION

The invention is in the field of analytical methods suitable for biochemical applications and provides a method for determining the amino acid sequence of a peptide as well as a method for digesting a protein in a gel. The determination of amino acid sequences of proteins and peptides is useful in the study of biological systems.

BACKGROUND OF THE INVENTION

The large scale study of structure and function of proteins and peptides is often termed proteomics. Proteins are vital parts of living organisms, as they are the main components of most physiological pathways in cells. The term "proteomics" was coined to make an analogy with genomics, the study of genes. The word "proteome" is a portmanteau of "protein" and "genome". The proteome of an organism is the set of proteins that are produced by the organism during its life, and its genome is its total set of genes.

Proteomics is often considered the next step in the study of biological systems, after genomics. The genome contains all the information required to construct an organism's protein compliment. However, proteomics is much more complicated than genomics, mostly because while an organism's genome is rather constant, a proteome differs from cell to cell and constantly changes via biochemical interactions dictated by its immediate environment. One organism has the same genome in nearly every cell, nevertheless, it may have a radically different protein expression profile in different parts of its body, different stages of its life cycle and different environmental conditions. Another major difficulty is the complexity of proteins relative to genes. For example, the human genomes consists of approximately 25 000 genes but it is estimated that more than 500 000 proteins can be derived from these genes. This increased complexity derives from mechanisms such as alternative splicing, post-translational protein modification (such as glycosylation or phosphorylation) and protein degradation.

Since proteins play a central role in the life of an organism, proteomics is instrumental in discovery of biomarkers, components that can indicate a particular disease. Current research in proteomics requires that the primary sequence of proteins be resolved, sometimes on a massive scale.

Many techniques have been developed for protein sequencing, including deriving the amino acid sequence from a DNA or RNA sequence or directly from the protein itself, such as Edman degradation or analysis by Mass Spectrometry. Nowadays, Mass spectrometry seems the method of choice for direct protein sequencing and a typical proteomics analysis may consist of the following five stages.

In stage 1, the proteins to be analysed are isolated from a biological source such as a cell lysate or tissue for instance by biochemical fractionation or affinity selection. This stage often includes a final step of two-dimensional gel electrophoresis, which usually separates proteins first by isoelectric point and then by molecular weight. Protein spots in a gel can be visualized using a variety of chemical stains or fluorescent markers. Proteins can often be quantified by the intensity of their stain. Once proteins are separated and quantified, they may be identified. Individual spots are cut out of the gel so that they contain a purified single protein species. The mass spectrum analysis of whole proteins is less sensitive than that of smaller peptides and the mass and charge of the intact protein by itself is insufficient for the identification of its primary amino acid sequence. Mass spectrometry can, in principle, sequence any size of protein, but the problem becomes computationally more difficult as the size increases. Proteolytic peptides are also easier to prepare for mass spectrometry than whole proteins, because they are more soluble. Therefore, proteins are preferably degraded into smaller proteolytic peptides in stage 2, for instance through enzymatic digestion. It should be noted that in certain cases, stage 1 may be omitted and the analyte of interest is directly subjected to stage 2.

In stage 2, degradation typically occurs enzymatically, for instance by trypsin digestion. Trypsin is a serine endoprotease found in the digestive system and catalyses the hydrolysis of peptide bonds, leading to proteolytic peptide fragments with C-terminally protonated amino acids. Trypsin predominantly cleaves proteins at the carboxyl side (or C-terminal side) of the amino acids lysine and arginine, except when either is followed by proline. In order to generate overlapping proteolytic peptide fragments, it is advantageous to use multiple enzymes with different specificities in this stage. Whereas trypsin is most commonly used, other enzymes employed for this purpose include pepsin, elastase, Lys-C, V8 (a Glu-C endoproteinase) and chymotrypsin.

In stage 3, the proteolytic peptide fragments are separated and delivered to the mass spectrometer. Separation may be achieved by one or more steps of liquid chromatography (LC) such as high-pressure liquid chromatography (HPLC) using narrow-bore (often below 100 micron) columns. One method of delivering the peptides to the spectrometer is electrospray ionization (ESI). At the end of the HPLC column, the solution is sprayed out of a narrow nozzle charged to a high positive potential into the mass spectrometer. The charge on the droplets causes them to fragment until only intact protonated proteolytic peptides remain, often termed peptide precursor ions. Matrix-assisted laser desorption/ionization (MALDI) is another technique commonly used to volatize and ionize the proteolytic peptides for mass spectrometric analysis. ESI ionizes the analytes out of a solution and is therefore readily coupled to liquid-based (for example, chromatographic and electrophoretic) separation tools, MALDI sublimates and ionizes the samples out of a dry, crystalline matrix via laser pulses. MALDI-MS is normally used to analyze relatively simple peptide mixtures, whereas integrated liquid-chromatography ESI-MS systems (LC-MS) are preferred for the analysis of complex samples.

In stage 4, a mass spectrum of the peptides eluting at a particular time point is taken (MS1 spectrum, or 'normal mass spectrum'). Mass spectrometric measurements are carried out in the gas phase on ionized analytes (protonated proteolytic peptides, peptide precursor ions). By definition, a mass spectrometer consists of an ion source, a mass analyser that measures the mass-to-charge ratio (m/z) of the ionized analytes, and a detector that registers the number of ions at each m/z value.

In stage 5, the computer generates a prioritized list of these peptide precursor ions for fragmentation and a series of tandem mass spectrometric or 'MS/MS' analyses ensues. The first stage of tandem MS/MS isolates individual peptide precursor ions, and the second breaks the peptide precursor ions into peptide fragment ions and uses the fragmentation pattern to determine their amino acid sequences. The MS and MS/MS spectra are typically acquired for about one second each and stored for matching against protein sequence databases.

The outcome of the analysis is the amino acid sequence of the proteolytic peptide fragments and therefore the peptides and proteins making up the (purified) protein population.

In mass spectrometry, collision-induced dissociation (CID), referred to by some as collisionally activated dissociation (CAD), is currently the method of choice. CID is a mechanism by which to fragment peptide precursor ions in the gas phase. The peptide precursor ions are usually accelerated by some electrical potential to high kinetic energy in the vacuum of a mass spectrometer and then allowed to collide with neutral gas molecules (often helium, nitrogen or argon). The collisions allow some of the kinetic energy to be converted into internal energy which results in bond breakage and the fragmentation of the peptide precursor ion into smaller fragments. These fragment ions can then be analyzed by a mass spectrometer.

CID is frequently used as part of tandem mass spectrometry in proteomics analyses. While CID is currently the most popular method for standard tandem mass spectrometry, there are also other fragmentation methods, for example electron transfer dissociation (ETD) and electron capture dissociation (ECD).

These different fragmentation techniques lead to the appearance of different types of ion fragments. A nomenclature for various ion types was first suggested by P. Roepstorff and J. Fohlman (Proposal for A Common Nomenclature for Sequence Ions In Mass-Spectra of Peptides. Biomed. Mass Spectrom. 11, 601-601 (1984)) and subsequently modified as described by K. Biemann (Contributions of Mass-Spectrometry to Peptide and Protein-Structure. Biomed. and Env. Mass Spectrom. 16, 99-111 (1988)). Typically y, b (cleavage of the peptide bond) and a fragments (formally a loss of CO from a b ion) are observed in CID. This is schematically depicted in FIG. 1.

ECD is usually considered a more direct fragmentation technique as compared to CID. In contrast to CID, ECD involves the introduction of low energy electrons to trapped gas phase ions. ECD produces significantly different types of fragment ions than CID. The unique (and complementary) fragments observed and the ability to fragment whole macromolecules effectively has been considered the most promising features of ECD. However, the low efficiencies and other technical difficulties have prevented wide spread use. ECD is primarily used in Fourier transform ion cyclotron resonance mass spectrometry.

ETD does not use free electrons but employs radical anions such as for example anthracene or azobenzene. When these anions react with positively charged peptide precursor ions an electron is transferred leading to the formation of c and z peptide fragment ions (FIG. 1). ETD cleaves peptide bonds randomly along the peptide backbone while side chains and modifications such as phosphorylation are usually left intact. The technique works well for higher charge state ions ($z>2$).

Analysis of some post-translational modifications (PTMs), such as phosphorylation, sulfonation, and glycosylation, is difficult with CID since the modification is often labile and preferentially lost over peptide backbone fragmentation, resulting in little to no peptide sequence information. The presence of multiple basic residues also makes peptides exceptionally difficult to sequence by conventional CID mass spectrometry. In a recent review, the utility of ETD mass spectrometry for sequence analysis of post-translationally modified and/or highly basic peptides was investigated (Molina et al., Proceedings of the National Academy of Sciences of the United States of America 104, (2007) 2199-2204). Phosphorylated, sulfonated, glycosylated, nitrosylated, disulfide bonded, methylated, acetylated, and highly basic peptides were analyzed by CID and ETD mass spectrometry. It was concluded that ETD is an excellent method for localization of phosphorylation sites. This illustrates the utility of ETD as an advantageous tool in phosphoproteomics research.

Protein identifications using peptide CID spectra are more clear-cut than those achieved by mass mapping because, in addition to the peptide mass, the peak pattern in the CID spectrum also provides information about peptide sequence.

This information however, is not readily convertible into a full, unambiguous peptide sequence, therefore, CID is generally considered not very suitable for automated de novo sequencing. Instead, the CID spectra are scanned against comprehensive protein sequence databases using one of a number of different algorithms, each with its strengths and weaknesses.

The 'peptide sequence tag' approach extracts a short, unambiguous amino acid sequence from the peak pattern that, when combined with the mass information, is a specific probe to determine the origin of the peptide.

In the 'cross-correlation' method, peptide sequences in the database are used to construct theoretical mass spectra and the overlap or 'cross-correlation' of these predicted spectra with the measured mass spectra determines the best match.

In the third main approach, 'probability based matching', the calculated fragments from peptide sequences in the database are compared with observed peaks. From this comparison a score is calculated which reflects the statistical significance of the match between the spectrum and the sequences contained in a database.

In each of these methods the identified peptides are compiled into a protein 'hit list', which is the output of a typical proteomic analysis. Because protein identifications rely on matches with sequence databases, high-throughput proteomics is currently restricted largely to those species for which comprehensive sequence databases are available.

For those species where no genomic sequence information is available, amino acid sequencing can only be done "de novo". i.e. without database matching. The spectra usually obtained in the above described prior art methods are hardly if at all suited for de novo sequencing since they do not provide unambiguous and easy to read sequence information.

The present invention addresses this problem and provides a method for determining the amino acid sequence of a peptide wherein MS spectra are produced with very clear and unambiguous sequence information which is interpretable without the help of comprehensive databases. The method according to the invention provides MS/MS spectra containing predominantly c ions in sequential order. The method according to the invention is therefore particularly suited for de novo sequencing. Moreover, it provides an improved method for the analysis of post-translational modifications of proteins.

SUMMARY OF THE INVENTION

The invention relates to a method for determining at least part of the amino acid sequence of a protein comprising the steps of cleaving the protein into proteolytic peptides, ionizing the proteolytic peptides to generate peptide precursor ions, dissociating these peptide precursor ions using tandem mass spectrometry in order to obtain peptide fragment ions, followed by determining the amino acid sequence of a selected proteolytic peptide, wherein the cleaving step generates at least one proteolytic peptide with an N-terminal lysine residue and wherein the dissociation of the peptide precursor ions is initiated by electron transfer.

In other words, the invention relates to the use of electron transfer dissociation in tandem mass spectrometry-based protein sequencing of proteolytic peptides with an N-terminal Lysine residue.

The method and use according to the invention may advantageously be performed using an N-terminal Lysine-specific endoprotease.

It was also found that part of the method according to the invention may be performed on a slice from a gel. The invention therefore also relates to a method for digesting a protein or peptide in a gel, comprising the steps of isolating a specific slice of the gel containing the protein or peptide and incubating the specific slice with an N-terminal Lysine-specific endoprotease in order to obtain proteolytic peptides.

DETAILED DESCRIPTION OF THE INVENTION

Peptide sequencing via tandem mass spectrometry (MS/MS) is one of the most powerful tools in proteomics for identifying proteins. Because complete genome sequences are accumulating rapidly, the recent trend in interpretation of MS/MS spectra has been through database search. However, de novo MS/MS spectral interpretation remains an open problem typically involving manual interpretation by expert mass spectrometrists. Several new algorithms have been developed for de novo interpretation that automatically learn fragment ion types and intensity thresholds from a collection of test spectra generated from any type of mass spectrometer (Dancik et al., J. Comp. Biol. 6, 327-342 (1999) and Performance Evaluation of Existing De Novo Sequencing Algorithms; Sergey Pevtsov, Irina Fedulova, Hamid Mirzaei, Charles Buck, and Xiang Zhang J. Proteome Res., 5 (11), 3018-3028, (2006)).

In a few seconds, a tandem mass spectrometer is capable of ionizing a mixture of proteolytic peptides with different sequences and measuring their respective parent mass/charge ratios, selectively fragmenting each peptide into pieces and measuring the mass/charge ratios of the fragment ions. The peptide sequencing problem is then to derive the sequence of the peptides given their MS/MS spectra.

For an ideal fragmentation process and an ideal mass spectrometer the sequence of a peptide could be simply determined by converting the mass differences of consecutive ions in a spectrum to the corresponding amino acids. This ideal situation would occur if the fragmentation process could be controlled so that each peptide was cleaved between every two consecutive amino acids and a single charge was retained on only the N-terminal piece. In practice, the fragmentation processes in mass spectrometers are far from ideal. As a result, de novo peptide sequencing remains an open problem and even a simple spectrum may require tens of minutes for a trained expert to interpret.

In contrast to database searching, de novo sequencing allows to derive the peptide sequence directly from the mass spectrum. De novo sequencing becomes a necessity, if a peptide is not present in any database. The main application of de novo sequencing is for the study of non-sequenced organisms, detecting mutated peptides and post-translational modifications.

The main problem with standard (low mass accuracy, one fragmentation technique) de novo sequencing is the inability to distinguish the direction of the fragments (N- or C-terminal), and the low mass accuracy which leads to an excessive number of potential solutions.

Many different de novo sequencing approaches have been suggested over the years. The simplest and most exhaustive approach is permutation of all conceivable amino acid combinations possible for a given peptide mass, and generation of theoretical mass spectra for each combination, "global approach". This is followed by comparison of all candidates with the real mass spectrum and selection of the best match.

Often, especially for low mass accuracy data, several theoretical spectra corresponding to different sequences will give an equally good match with the experimental spectrum. In many cases this is due to the fact that the b and y ion and/or c and z ion of a given sequence coincide in mass within the given mass accuracy.

Several groups have explored alternative proteases for MS/MS analysis of proteolytic peptides (Molina et al., Proceedings of the National Academy of Sciences of the United States of America 104 (7), 2199 (2007) and Garcia et al., Journal of Proteome Research 3 (6), 1219 (2004)). They explored the utility of Lys-C, Trypsin and Glu-C using CID and ETD and concluded that, for ETD applications, Lys-C offered a useful alternative to trypsin for the analysis of post-translational modifications in phosphoproteins.

Rao et al. demonstrated that a peptidyl-Lys metalloendoprotease could be used for the $^{18}O$ in vitro labeling of proteolytic peptides and argued its usefulness in comparative proteomic studies (J. Proteome Research 4, 507-514 (2005) and Molec. Cell. Proteomics 4. 1550-1557 (2005)). They showed two CID MS/MS spectra of peptides with an N-terminal lysine residue. These spectra consisted of a typical CID pattern of b and y ions with a complexity that was not particularly suitable for de novo sequencing.

The term "Lys-N" as well as "endoproteases with N-terminal lysine cleavage specificity" is used herein to indicate a protein from the EC class 3.4.24.20 that cleaves peptidyl-lysine bonds (-X-Lys- in proteins and peptides).

Surprisingly, we now found that endoproteases with N-terminal Lysine (Lys-N) cleavage specificity were very suitable for de novo sequencing when used in combination with electron transfer dissociation (ETD) because this combination yielded straightforward and easy-to-interpret MS/MS spectra.

The MS/MS spectra generated with a method according to the invention consisted predominantly, if not exclusively of c-ions and presented those c-ions in consecutive order, thereby greatly facilitating de novo sequencing of the proteolytic peptides. Statistical analysis of the properties for the spectra obtained with LysN in combination with ETD indicate, that on average more than 90% of identified peaks are c-ions. The invention therefore also relates to a method as described above wherein the tandem mass spectrometry results in a spectrum wherein on average more than 90% of identified peaks are c-ions, preferably more than 95% or even more preferably 100%.

In comparison to the use of Lys-C and trypsin, comparable specificity, sensitivity and selectivity were found for Lys-N proteases. Surprisingly, cleavage of peptides at the N terminus of a Lysine residue provided a clear advantage over other proteases due to the fact that the peptide ETD MS/MS spectra obtained with Lys-N consisted almost exclusively of c-type fragment ions.

Such clear spectra, providing simple sequence ladders, may prove to be a valuable strategy for the de novo sequence analysis of proteolytic peptides, such as for those peptides carrying post-translational modifications. The product ion statistics, mentioned above, allow development of computational efficient search algorithms for identifying peptides from the spectra obtained with LysN in combination with ETD.

Hence, the invention relates to the use of electron transfer dissociation in tandem mass spectrometry-based protein sequencing of proteolytic peptides with an N-terminal lysine residue.

In more detail, the invention may be described as a method for determining at least part of the amino acid sequence of a protein comprising the steps of cleaving the protein into proteolytic peptides, ionizing the proteolytic peptides to generate peptide precursor ions, dissociating these peptide precursor ions using tandem mass spectrometry in order to obtain peptide fragment ions, followed by determining the amino acid sequence of a selected proteolytic peptide, wherein the cleaving step generates at least one proteolytic peptide with an N-terminal lysine residue and wherein the dissociation of the peptide precursor ions is initiated by electron transfer.

Advantageously, the cleavage step is performed by an enzyme.

In the Examples section, two different metalloendoproteases are exemplified that contain one atom of zinc per molecule, and which both generate N-terminal lysine fragments. The invention therefore relates to a method as described above wherein the enzyme is a metalloendopeptidase.

Enzymes may favorably be specific for an acyl-lysine bond; hence the method according to the invention may be described as a method wherein the enzyme is specific for an acyl-lysine bond. Such enzymes are categorized as EC 3.4.24.20, official name Peptidyl-Lys metalloendopeptidase.

Such enzymes may also favorably be obtained from a fungus (Nonaka et al., J. Biol. Chem. 272 (1997) 30032-30039). The invention therefore also concerns a method as described above wherein the enzyme is obtainable from a fungus. Enzymes having the amino acid sequence according to SEQ ID NO: 1 or SEQ ID NO: 2 (FIG. 6) obtainable from the fungi *Grifola frondosa* and *Pleurotus ostreatus* respectively, are preferred since they performed well in the method according to the invention.

Now that it is disclosed herein that the enzymes as described above may favorably be used for ETD MS/MS-based peptide sequencing, it is evident that alternative methods may be found by searching databases and screening other organisms for enzymes that have Lys-N specificity.

Such enzymes may be found by searching for nucleic acids with substantial homology with the sequences as disclosed herein (SEQ ID NO: 1 and SEQ ID NO: 2).

It is to be expected that enzymes with at least 85% sequence homology to SEQ ID NO: 1 or SEQ ID NO: 2 will perform at least equally well as the enzymes disclosed herein. Preferably, the homology is more than 90%, such as 92, 95, 96, 97, 98 or even more than 99%.

A nucleic acid or fragment thereof is "substantially homologous" ("or substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95-98% of the nucleotide bases.

Alternatively, substantial homology or (similarity) exists when a nucleic acid or fragment thereof will hybridize to another nucleic acid (or a complementary strand thereof) under selective hybridization conditions, to a strand, or to its complement. Selectivity of hybridization exists when hybridization which is substantially more selective than total lack of specificity occurs. Typically, selective hybridization will occur when there is at least about 55% homology over a stretch of at least about 14 nucleotides, preferably at least about 65%, more preferably at least about 75%, and most preferably at least about 90%. See, Kanehisa, 1984. The length of homology comparison, as described, may be over longer stretches, and in certain embodiments will often be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30 degrees Celsius. typically in excess of 37 degrees Celsius., and preferably in excess of 45 degrees Celsius. Stringent salt conditions will ordinarily be less than 1000 mM, typically less than 500 mM, and preferably less than 200 mM. However, the combination of parameters is much more important than the measure of any single parameter. See, e.g., Wetmur & Davidson, 1968. Suitable protocols for performing hybridisation experiments can be found in Sambrook et al. 2000. Molecular Cloning: A Laboratory Manual (Third Edition) Cold Spring Harbor Laboratory Press.

Methods for determining sequence homology between different strands of nucleic acids or proteins are known in the art. Homology is typically measured using sequence analysis software. See, e.g., the Sequence Analysis Software Package of the Genetics Computer Group, University of Wisconsin Biotechnology Center, 910 University Avenue, Madison, Wis. 53705. Protein analysis software matches similar sequences using measure of homology assigned to various substitutions, deletions and other modifications. Conservative substitutions in amino acid sequences typically include substitutions within the following groups: glycine, alanine; valine, isoleucine, leucine; aspartic acid, glutamic acid; asparagine, glutamine; serine, threonine; lysine, arginine; and phenylalanine, tyrosine.

The invention therefore relates to a method as described above wherein the enzyme has an amino acid sequence derived from a DNA sequence which is substantially homologous to a DNA sequence encoding the polypeptides as disclosed herein (SEQ ID NO: 1 and SEQ ID NO: 2).

The invention also relates to a method as described above wherein the enzyme has an amino acid sequence having at least 85% homology to the amino acid sequence of a *Grifola frondosa* metalloendopeptidase according to SEQ ID NO: 1 or of a *Pleurotus ostreatus* metalloendopeptidase according to SEQ ID NO: 2.

Improved enzymes may be obtained by mutating the DNA sequences encoding the amino acid sequences of SEQ ID NO: 1 or SEQ ID NO: 2 and selecting for enzymes with improved stability, specificity, or other desirable characteristics.

Figure 2:
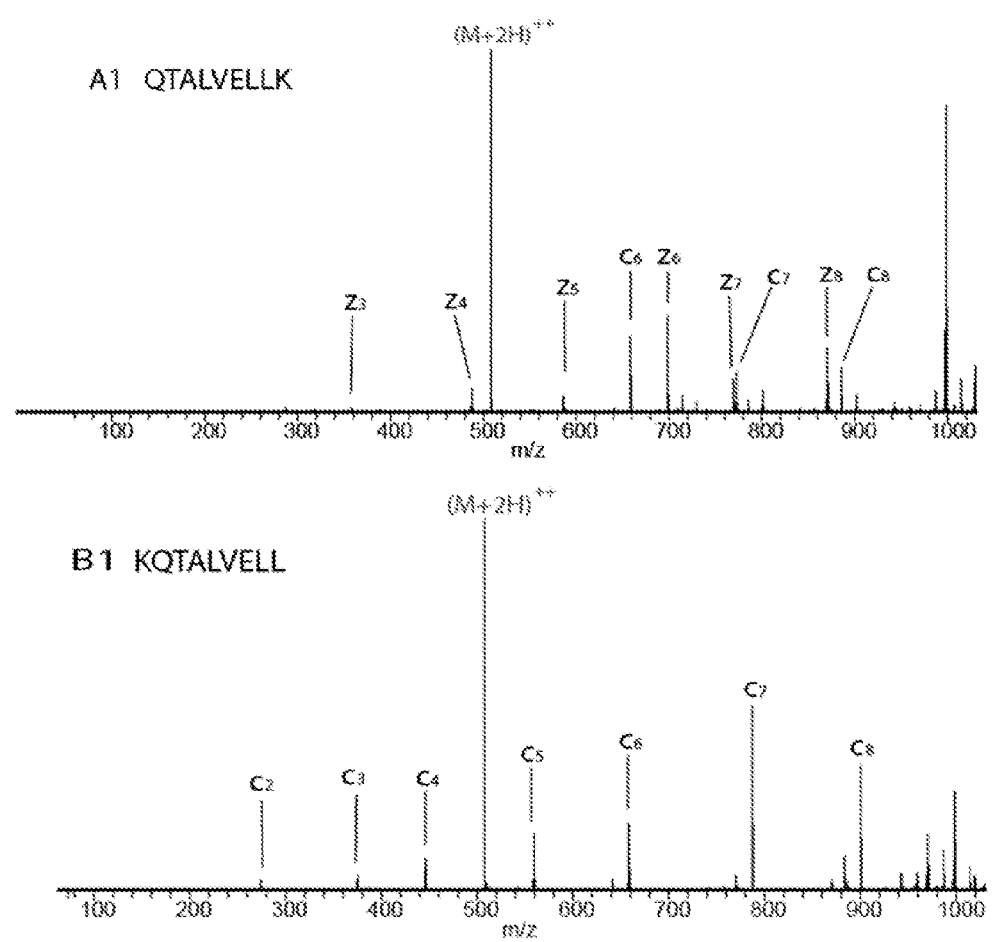

In a comparative experiment (example 4), Lys-C generated proteolytic peptides of BSA were subjected to ETD. In FIG. 2, the resulting ETD induced fragmentation spectrum is given (spectrum A), which revealed the formation of multiple c and z peptide fragment ions with the z ions marginally being more dominant.

In parallel, the performance of a Lys-N endopeptidase was evaluated under the same experimental conditions, i.e. on BSA with analysis by ETD. When the Lys-N proteolytic peptides were subjected to ETD, the only peptide fragment ions observed were N-terminal c ions, as depicted in FIG. 2, spectrum B. Most notably, these c-ions were displayed in consecutive order.

Figure 3:
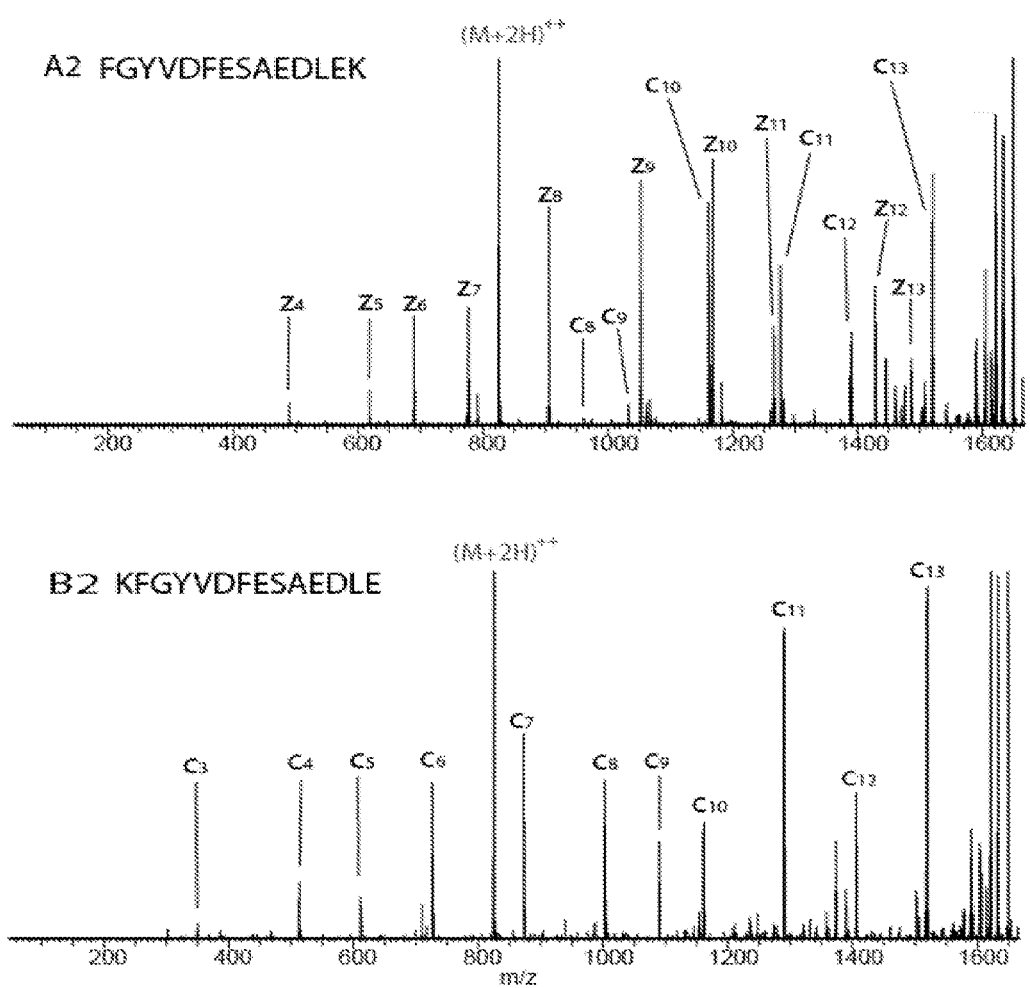

To test the general applicability of Lys-N and its feasibility for biological samples, a whole cell lysate of HEK 293 cells was digested in parallel with Lys-N and Lys-C. The generated complex peptide mixtures were analyzed by ETD. In FIG. 3, spectrum A2 shows a typical peptide fragmentation obtained for a Lys-C generated proteolytic peptide, whereas spectrum B2 originated from a Lys-N peptide. These findings are quite similar to the above findings and resemble those observed for BSA (FIG. 2), namely a dominance of c ions in consecutive order in the spectrum obtained with Lys-N.

Figure 4:
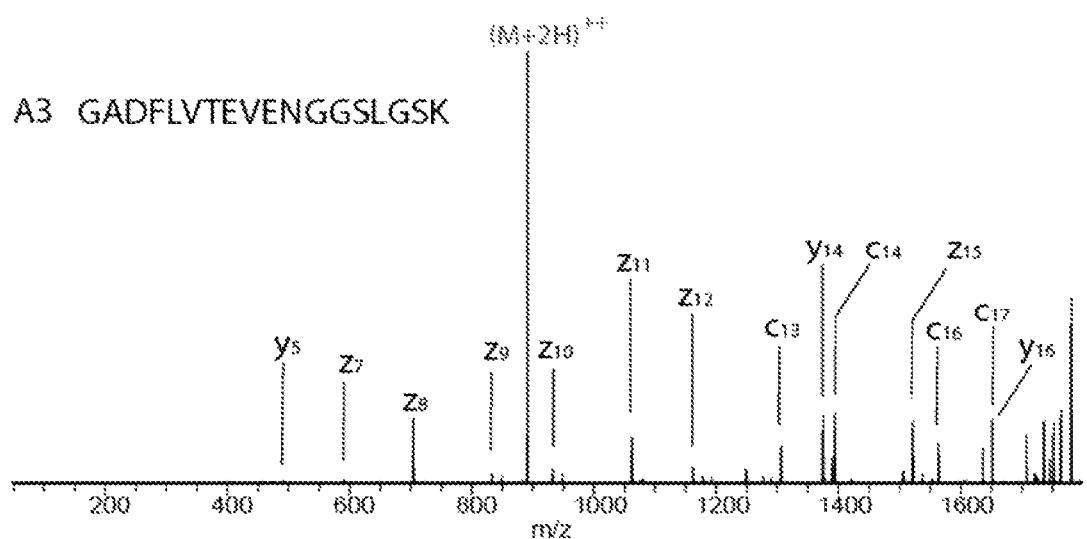
Figure 4:
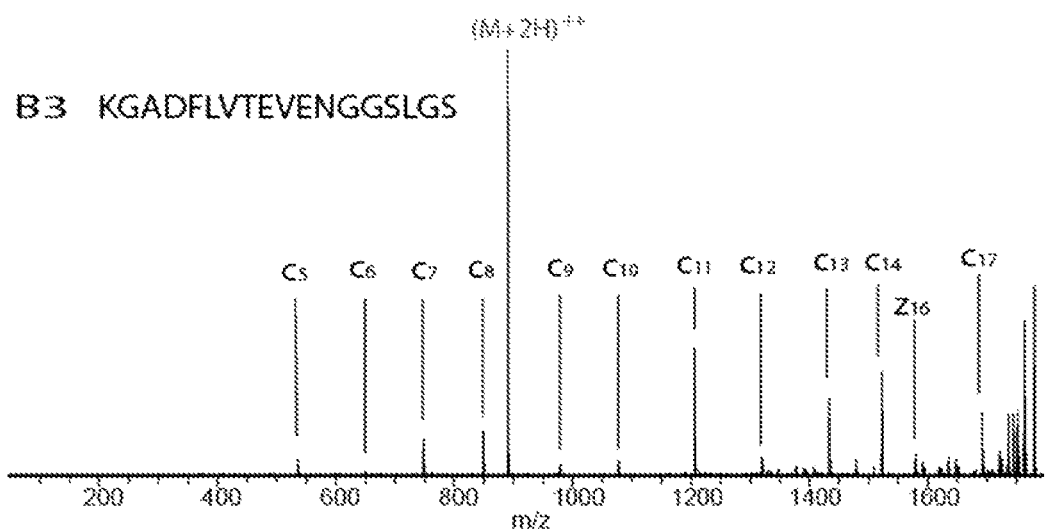

Yet another peptide obtained from a whole cell lysate of HEK 293 cells was digested in parallel with Lys-N and Lys-C and analyzed by ETD. In FIG. 4, spectrum A3 shows a typical peptide fragmentation obtained for a Lys-C generated peptide, whereas spectrum B3 originated from a Lys-N peptide. Again, this confirmed the above findings and showed a spectrum with predominantly c-ions (one z-ion was identified) with the c-ions in consecutive order.

Summarizing, using Lys-N in combination with ETD we observed cleavage at almost every amide bond in the peptide backbone, providing easy to interpret sequence ladders.

Without wanting to be bound by theory, the following is provided as an ex post facto analysis of a possible mechanism underlying the observed advantages of Lys-N. Lys-C generated peptides have a basic entity at both termini. Therefore, the fragmentation of Lys-C generated peptides may result in the formation of both c and z type ions under ETD conditions. In contrast, in Lys-N generated peptides the protons or charges will be preferentially attached to the N-terminus due to the presence of two free amine groups, which may result in the exclusive generation of c-type fragment ions.

The above experiments showed that the Lys-C enzyme yielded peptide fragment that dissociated under ETD conditions into a complex mixture containing about equal amounts of both c- and z-ions. As a consequence, the MS/MS spectra were more difficult to interpret. In contrast, the spectra obtained with Lys-N generated peptides were solely dominated if not exclusively formed by c-ion sequence ladders and were therefore easier to interpret. This is considered a huge advantage for de novo sequencing of proteins and peptides.

We also compared the performance of Lys-N generated proteolytic peptides in ETD and CID. As expected, the Lys-N proteolytic peptides resulted in a spectrum consisting of a mixture of b and y ions when CID was used for the ionization of the proteolytic peptides. However, when ETD was used, this resulted in nice clean sequence ladders of c-ions without any z ions present. This is illustrated in the representative example shown in FIG. 5.

In addition, protein analyses may also be performed on analytes that originate from one and two-dimensional sodium-dodecylsulphate-polyacrylamide gel electrophoresis (SDS-PAGE) separations as well as on iso-electrofocussing gel separations. We again tested the applicability of the Lys-N protease to proteins (i.e. BSA) after being migrated through a gel. As Lys-C is known to be less well adaptable to protein spots from gels, we compared the performance of Lys-N with trypsin.

Surprisingly, Lys-N proved to be at least as efficient as trypsin for in-gel proteolysis, as evidenced in table 1. Consequently, the invention relates to a method for digesting a protein or peptide in a gel, comprising the steps of isolating a specific slice of the gel containing the protein or peptide and incubating the specific slice with an N-terminal Lysine-specific endoprotease in order to obtain proteolytic peptide fragments. Preferred are such methods wherein the enzyme is a metalloendopeptidase, preferably with specificity for an acyl-lysine bond.

In such a method, gels may preferably be selected from the group consisting of one-dimensional gels, two-dimensional gels, polyacrylamide gels, iso-electric focusing gels

TABLE 1

| Enzyme | Suitable for in-gel digestion | Obtained sequence coverage | Number of identified peptide fragments | Number of peptides dominated by c-ions | Required protease/protein ratio |
|---|---|---|---|---|---|
| Trypsin | YES | | | | |
| Lys-C | NO | 59% | 28 | 0% (0/19) | 1:50 |
| Lys-N | YES | 56% | 27 | 100% (14/14) | 1:85 |

Table 1: One-to-One Comparison of Lys-C and Lys-N.

This comparison was made using BSA as model protein. The amount of proteases needed, the obtained sequence coverage, and the number of identified peptide fragments are similar. However, as described herein, the ETD MS/MS spectra were dominated by c-ions for the Lys-N peptides. Moreover, Lys-N is suitable for in-gel digestion.

Reagents for biochemical methods are often commercially obtainable in the form of a kit of parts. Such kits then contain the reagents in combination with a product insert that describes the envisaged use of the parts. The method according to the invention may therefore be provided in the form of a kit for degrading a protein into proteolytic peptides, containing at least an N-terminal Lysine-specific endoprotease and a manual for digesting a protein or peptide in order to make it suitable for tandem mass spectrometry-based protein sequencing in combination with electron transfer dissociation.

In conclusion, in this study we evaluated a Lys-N protease for ETD MS/MS proteomics analyses. In general, as far as sensitivity, selectivity and specificity are concerned; the Lys-N protease performs at least equally well as currently used proteases. Remarkably, we found that Lys-N provides a clear advantage over other proteases due to the fact that the peptide ETD MS/MS spectra almost exclusively consisted of c-type fragment ions, resulting in simple-to-read sequence ladders for the peptides of interest. It was found that Lys-N, in combination with ETD, therefore provides a valuable strategy for the analysis of post-translational modifications and de novo sequencing. Moreover, Lys-N was found to be suitable for in-gel digestion.

The following literature describes useful background information and is herewith incorporated by reference.

REFERENCES 1. 1H. Kang, L. Pasa-Tolic, and R. D. Smith, Journal of the American Society for Mass Spectrometry 18 (7), 1332 (2007);
2. P. Mallick, M. Schirle, S. S. Chen et al., Nature Biotechnology 25 (1), 125 (2007).
3. A. I. Nesvizhskii, O. Vitek, and R. Aebersold, Nature methods 4 (10), 787 (2007);
4. Shevchenko, M. Wilm, O. Vorm et al., Analytical Chemistry 68 (5), 850 (1996).
5. K. G. Standing, Current opinion in structural biology 13 (5), 595 (2003).
6. T. Keough, R. S. Youngquist, and M. P. Lacey, Proceedings of the National Academy of Sciences of the United States of America 96 (13), 7131 (1999).

7. E. C. Peters, D. M. Horn, D. C. Tully et al., Rapid Communications in Mass Spectrometry 15 (24), 2387 (2001).
8. J. E. P. Syka, J. J. Coon, M. J. Schroeder et al., Proceedings of the National Academy of Sciences of the United States of America 101 (26), 9528 (2004);
9. Y. Xia, H. P. Gunawardena, D. E. Erickson et al., Journal of the American Chemical Society (2007);
10. R. A. Zubarev, N. L. Kelleher, and F. W. McLafferty, Journal of the American Chemical Society 120 (13), 3265 (1998);
11. A. Chi, D. L. Bai, L. Y. Geer et al., International Journal of Mass Spectrometry 259 (1-3), 197 (2007);
12. L. M. Mikesh, B. Ueberheide, A. Chi et al., Biochimica et biophysica acta 1764 (12), 1811 (2006).
13. H. Molina, D. M. Horn, N. Tang et al., Proceedings of the National Academy of Sciences of the United States of America 104 (7), 2199 (2007).
14. B. A. Garcia, S. A. Busby, C. M. Barber et al., Journal of Proteome Research 3 (6), 1219 (2004).
15. E. S. Witze, W. M. Old, K. A. Resing et al., Nature methods 4 (10), 798 (2007).
16. V. H. Wysocki, G. Tsaprailis, L. L. Smith et al., Journal of Mass Spectrometry 35 (12), 1399 (2000).
17. D. L. Swaney, G. C. McAlister, M. Wirtala et al., Analytical Chemistry 79 (2), 477 (2007);
18. N. Leymarie, C. E. Costello, and P. B. O'Connor, Journal of the American Chemical Society 125 (29), 8949 (2003).
19. H. L. Han, Y. Xia, and S. A. McLuckey, Journal of Proteome Research 6 (8), 3062 (2007).
20. R. E. March, Journal of Mass Spectrometry 32 (4), 351 (1997).

LEGEND TO THE FIGURES

FIG. 1: Nomenclature for various ion types

FIG. 2: Schematic representation of the ETD induced fragmentation in Lys-C and Lys-N generated doubly charged peptide ions and ETD MS/MS spectra of doubly charged ions originating from A1) Lys-C and B) Lys-N generated peptides from BSA (A) QTALVELLK (SEQ ID NO:3) and (B1) KQTALVELL (SEQ ID NO:4). The spectrum in the B panel shows a nearly complete sequence ladder of c-ions.

FIG. 3: Schematic representation of the ETD induced fragmentation in Lys-C and Lys-N generated doubly charged peptide ions and ETD MS/MS spectra of doubly charged ions originating from A2) Lys-C and B2) Lys-N generated peptides from HEK293 cells. (A2) FGYVDFESAEDLEK (SEQ ID NO:5) and (B2) KGYVDFESAEDLE (SEQ ID NO:6). The spectrum in the B2 panel shows a nearly complete sequence ladder of c-ions.

FIG. 4: Schematic representation of the ETD induced fragmentation in Lys-C and Lys-N generated doubly charged peptide ions and ETD MS/MS spectra of doubly charged ions originating from A3) Lys-C and B3) Lys-N generated peptides from HEK293 cells. (A3) GADFLVTEVENGGSLGSK (SEQ ID NO:7) and (B3) KGADFLVTEVENGGSLGS (SEQ ID NO:8). The spectrum in the B3 panel shows a nearly complete sequence ladder of c-ions.

Figure 5:
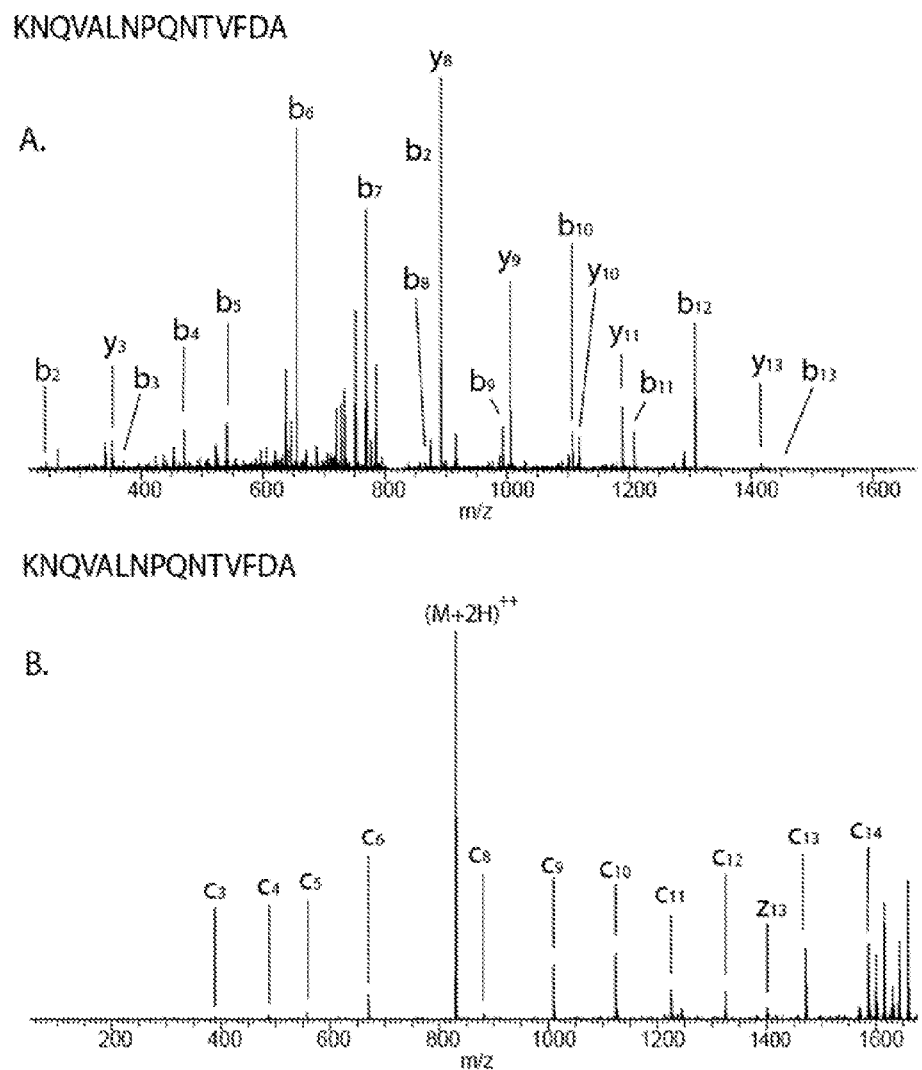

FIG. 5: Typical CID and ETD MS/MS spectra of a Lys-N generated doubly charged peptide ion. (A) CID mass spectrum of Lys-N generated KNQVALNPQNTVFDA (SEQ ID NO:9). (B) ETD mass spectrum of Lys-N generated KNQVALNPQNTVFDA (SEQ ID NO:10). Typically, the ETD spectra are much easier to interpret and provide straightforward sequence ladders.

EXAMPLES

Example 1

Materials and Methods

Protease inhibitor cocktail and Lys-C were obtained from Roche Diagnostics (Mannheim. Germany). Metalloendopeptidase from *Grifola Frondosa* (Lys-N) was obtained from Seikagaku Corporation (Tokyo, Japan). Alternatively, a metalloendopeptidase from *Pleurotus ostreatus* may be used (Nonaka et al., J. Biol. Chem. 272 30032-30039 (1997)). Bovine Serum Albumin (BSA) and Iodoacetamide were obtained from Sigma-Aldrich (Steinheim, Germany). DL-Dithiothreitol was obtained from Fluka biochemical (Steinheim, Germany). HEK293 cells were a gift from the ABC Protein Expression Center (Utrecht University, The Netherlands). HPLC-S gradient grade acetonitrile was purchased from Biosolve (Valkenwaard, The Netherlands). Acetic acid was obtained by MERCK KGaA (Damstadt, Germany) and high purity water obtained from Milli-Q system (Millipore, Bedford, Mass.).

Human Embryonic kidney (HEK) 293T cells (HEK293 cells) were harvested at a density of approx $1.5 \times 10^6$ cells/mL and stored at $-30°$ C. Cells were thawed and resuspended in ice-cold lysisbuffer (15 mL PBS, 150 µl Tween 20 and protease inhibitor cocktail). After Dounce homogenizing on ice, the lysate was stored at $0°$ C. for 10 min. Subsequently centrifugation at 20000×g in a tabletop centrifuge (Eppendorf, Hamburg, Germany) at $4°$ C. yielded separation of soluble and insoluble protein fractions. The soluble fraction was collected and the concentration determined by a Bradford assay. The lysate was dissolved in 50 mM ammonium bicarbonate to a concentration of 4 mg/mL.

Example 2

HEK293 Lysate and BSA in-Solution Digestion

Hundred mg digested protein/lysate was reduced with 45 mM dithiothreitol ($50°$ C., 15 min) followed by alkylation using 110 mM Iodoacetamide (dark, RT, 15 min). Buffer exchange was performed with 50 mM ammonium bicarbonate using 5 kD spin columns. The resulting solutions were dried in a vacuum centrifuge and resuspended in 50 mM ammonium bicarbonate. The purified digests were aliquoted. One part was digested with Lys-C and an equal amount with Lys-N. Lys-C was added to the samples at a 1:50 (w/w) ratio and incubated at $25°$ C. over night and Lys-N was added at a ratio of 1:85 (w/w) and also incubated over night at $25°$ C.

Example 3

BSA in Gel-Digestion

Gel bands containing BSA were cut out of the gel and washed with water. After shrinking the gel pieces with acetonitrile they were reduced with 10 mM of DTT ($60°$ C., 1 hour) followed by alkylation using 55 mM Iodoacetamide (dark, RT, min). After shrinking the gel pieces with acetonitrile they were incubated with trypsin or Lys-N (10 ng/µl) and left on ice for 30 min. Excess trypsin or Lys-N was then removed and enough AMBIC was added to cover the gel pieces. The gel pieces were incubated over night at $37°$ C. Supernatant was transferred to new eppendorf tubes. Peptide were extracted by adding 5% FA to the gel pieces following heating (65° C., 2 min) and shaking (RT, 20 min). The supernatant was added to the previous supernatant.

Example 4

CID and ETD Analysis

Digested BSA and HEK293 lysate were subjected to nanoscale liquid chromatography tandem mass spectrometry (nano-LC-MS/MS) analysis, performed on an Agilent 1100 HPLC system (Agilent Technologies) connected to a LTQ XL Linear Ion Trap Mass Spectrometer with an ETD source at the back from Thermo Fisher Scientific, Inc. (Waltham, Mass.). The samples (0.5 µg digested HEK293 lysate and 50 fmol of BSA) were diluted in 5% formic acid and injected on the trap column (Aqua C18 (phenomenex, Torrance, Calif.)), 20 mm×100 µm I.D.) at a flow rate of 5 µL/min. The peptides were transferred with a split-reduced flow rate of 100 nL/min solvent A (0.1 M acetic acid) onto an analytic column (Reprosil C18 RP (Dr Maisch, Germany), 20 cm×50 µm I.D.). Elution of peptides from digested lysate was achieved with a linear gradient from 0 to 35% B (acetonitrile/water (v/v) containing 0.1 M acetic acid) in 95 min and digested BSA was eluted with a linear gradient from 0 to 40% B in 45 min. The column effluent was directly introduced into the ESI source of the MS.

The mass spectrometer was operated in positive ion mode, from 350 to 1500 m/z in MS mode and with an AGC value of 1.00e+05. Parent ions were isolated for a more accurate mass measurement by performing a SIM scan and fragmented by CID or ETD in data-dependent mode with an AGC value of 1.00e+04.

Ions were fragmented using CID with normalized collision energy of 35 and 30 ms activation time. ETD fragmentation was performed with supplemental activation, fluoranthene was used as reagent anion and ion/ion reaction in the ion trap was taking place for 100 ms.

Example 5

Data Analysis

After MS measurements data was analyzed with the MASCOT software version 2.2.0 (on the world wide web at matrix-science.com). The database search was made with parameters set to consider a peptide tolerance of ±0.5 Da, a fragment tolerance of +0.9 Da, a static modification of +57 Da on cystein residues (Carbamidomethylation) and a differential modification of +16 Da on methionine (oxidation). CID and ETcaD spectra of digested lysate were searched in NCBInr 20070713 (5269953 sequences; 1825351362 residues) database and BSA in a BSA database.

The invention claimed is:

1. A method for determining at least part of the amino acid sequence of a protein; the method comprising:
    cleaving the protein into proteolytic peptides,
    ionizing the proteolytic peptides to generate peptide precursor ions,
    dissociating the peptide precursor ions utilizing tandem mass spectrometry in order to obtain peptide fragment ions, followed by
    determining the amino acid sequence of a selected proteolytic peptide,
wherein said cleaving results in at least one proteolytic peptide with an N-terminal lysine residue and wherein said dissociating of the peptide precursor ions utilizing tandem mass spectrometrcomprises electron transfer dissociation;
wherein the cleaving is performed by an enzyme specific for an acyl-lysine bond.

2. The method according to claim 1, wherein said enzyme is a metalloendopeptidase.

3. The method according claim 1, wherein said enzyme is a fungal enzyme.

4. The method according to claim 1, wherein said enzyme comprises an amino acid sequence having more than 85% homology to the amino acid sequence of SEQ ID NO: 1.

5. The method according to claim 1, wherein said step of determining the amino acid sequence of a selected proteolytic peptide is done de novo.

6. The method according to claim 1, wherein said enzyme comprises an amino acid sequence having more than 85% homology to the amino acid sequence of SEQ ID NO: 2.

7. A method of tandem mass-spectrometry based sequencing of peptides, the method comprising:
    providing peptides with an N-terminal lysine residue; and
    performing electron transfer dissociation on the peptides.

8. The method according to claim 7, wherein providing peptides with an N-terminal lysine residue comprises cleaving a protein with an enzyme specific for an acyl-lysine bond.

9. The method according to claim 8, wherein said enzyme is a fungal enzyme.

10. The method according claim 8, wherein said enzyme comprises an amino acid sequence having more than 85% homology to the amino acid sequence of SEQ ID NO: 1.

11. The method according claim 8, wherein said enzyme comprises an amino acid sequence having more than 85% homology to the amino acid sequence of SEQ ID NO: 2.

* * * * *

UNITED STATES PATENT AND TRADEMARK OFFICE
CERTIFICATE OF CORRECTION

| | |
|---|---|
| PATENT NO. | : 8,338,122 B2 |
| APPLICATION NO. | : 12/735373 |
| DATED | : December 25, 2012 |
| INVENTOR(S) | : Albert John Roeland Heck et al. |

It is certified that error appears in the above-identified patent and that said Letters Patent is hereby corrected as shown below:

In the claims:
CLAIM 1, COLUMN 17, LINE 58, change "spectrometrcomprises" to --spectrometry comprises--

Signed and Sealed this
Fifteenth Day of December, 2015

Michelle K. Lee
*Director of the United States Patent and Trademark Office*

SEQUENCE LISTING

<160> NUMBER OF SEQ ID NOS: 10

<210> SEQ ID NO 1
<211> LENGTH: 167
<212> TYPE: PRT
<213> ORGANISM: Grifola frondosa

<400> SEQUENCE: 1

Thr Tyr Asn Gly Cys Ser Ser Ser Glu Gln Ser Ala Leu Ala Ala Ala
1               5                   10                  15

Ala Ser Ala Ala Gln Ser Tyr Val Ala Glu Ser Leu Ser Tyr Leu Gln
            20                  25                  30

Thr His Thr Ala Ala Thr Pro Arg Tyr Thr Thr Trp Phe Gly Ser Tyr
        35                  40                  45

Ile Ser Ser Arg His Ser Thr Val Leu Gln His Tyr Thr Asp Met Asn
    50                  55                  60

Ser Asn Asp Phe Ser Ser Tyr Ser Phe Asp Cys Thr Cys Thr Ala Ala
65                  70                  75                  80

Gly Thr Phe Ala Tyr Val Tyr Pro Asn Arg Phe Gly Thr Val Tyr Leu
                85                  90                  95

Cys Gly Ala Phe Trp Lys Ala Pro Thr Thr Gly Thr Asp Ser Gln Ala
            100                 105                 110

Gly Thr Leu Val His Glu Ser Ser His Phe Thr Arg Asn Gly Gly Thr
        115                 120                 125

Lys Asp Tyr Ala Tyr Gly Gln Ala Ala Ala Lys Ser Leu Ala Thr Met
    130                 135                 140

Asp Pro Asp Lys Ala Val Met Asn Ala Asp Asn His Glu Tyr Phe Ser
145                 150                 155                 160

Glu Asn Asn Pro Ala Gln Ser
                165

```
<210> SEQ ID NO 2
<211> LENGTH: 168
<212> TYPE: PRT
<213> ORGANISM: Pleurotus ostreatus

<400> SEQUENCE: 2

Ala Thr Phe Val Gly Cys Ser Ala Thr Arg Gln Thr Gln Leu Asn Ala
1               5                   10                  15

Ala Ala Ser Gln Ala Gln Thr Tyr Ala Ala Asn Ala Leu Ser Tyr Leu
            20                  25                  30

Asn Ser His Thr Ser Ser Thr Thr Arg Tyr Thr Thr Trp Phe Gly Thr
        35                  40                  45

Phe Val Thr Ser Arg Tyr Asn Thr Val Leu Ser His Phe Ser Ser Ile
    50                  55                  60

Ser Ser Asn Thr Phe Ser Ser Tyr Thr Phe Asp Cys Thr Cys Ser Asp
65                  70                  75                  80

Ser Gly Thr Tyr Ala Phe Val Asn Pro Ser Asn Phe Gly Tyr Val Thr
                85                  90                  95

Leu Cys Gly Ala Phe Trp Asn Ala Pro Val Ala Gly Thr Asp Ser Arg
            100                 105                 110

Gly Gly Thr Leu Ile His Glu Ser His Phe Thr Arg Asn Gly Gly
        115                 120                 125

Thr Asp Asp His Val Tyr Gly Gln Ala Gly Ala Gln Ser Leu Ala Arg
    130                 135                 140

Ser Asn Pro Ala Gln Ala Ile Asp Asn Ala Asp Ser His Glu Tyr Phe
145                 150                 155                 160

Ala Glu Asn Asn Pro Ala Leu Ala
                165

<210> SEQ ID NO 3
<211> LENGTH: 9
<212> TYPE: PRT
<213> ORGANISM: Bos primigenius

<400> SEQUENCE: 3

Gln Thr Ala Leu Val Glu Leu Leu Lys
1               5

<210> SEQ ID NO 4
<211> LENGTH: 9
<212> TYPE: PRT
<213> ORGANISM: Bos primigenius

<400> SEQUENCE: 4

Lys Gln Thr Ala Leu Val Glu Leu Leu
1               5

<210> SEQ ID NO 5
<211> LENGTH: 14
<212> TYPE: PRT
<213> ORGANISM: Homo sapiens

<400> SEQUENCE: 5

Phe Gly Tyr Val Asp Phe Glu Ser Ala Glu Asp Leu Glu Lys
1               5                   10

<210> SEQ ID NO 6
<211> LENGTH: 13
<212> TYPE: PRT
<213> ORGANISM: Homo sapiens

<400> SEQUENCE: 6
```

```
Lys Gly Tyr Val Asp Phe Glu Ser Ala Glu Asp Leu Glu
1               5                   10

<210> SEQ ID NO 7
<211> LENGTH: 18
<212> TYPE: PRT
<213> ORGANISM: Homo sapiens

<400> SEQUENCE: 7

Gly Ala Asp Phe Leu Val Thr Glu Val Glu Asn Gly Gly Ser Leu Gly
1               5                   10                  15

Ser Lys

<210> SEQ ID NO 8
<211> LENGTH: 18
<212> TYPE: PRT
<213> ORGANISM: Homo sapiens

<400> SEQUENCE: 8

Lys Gly Ala Asp Phe Leu Val Thr Glu Val Glu Asn Gly Gly Ser Leu
1               5                   10                  15

Gly Ser

<210> SEQ ID NO 9
<211> LENGTH: 15
<212> TYPE: PRT
<213> ORGANISM: Homo sapiens

<400> SEQUENCE: 9

Lys Asn Gln Val Ala Leu Asn Pro Gln Asn Thr Val Phe Asp Ala
1               5                   10                  15

<210> SEQ ID NO 10
<211> LENGTH: 15
<212> TYPE: PRT
<213> ORGANISM: Homo sapiens

<400> SEQUENCE: 10

Lys Asn Gln Val Ala Leu Asn Pro Gln Asn Thr Val Phe Asp Ala
1               5                   10                  15
```